United States Patent [19]

Kranz et al.

[11] Patent Number: 4,981,481
[45] Date of Patent: Jan. 1, 1991

[54] MARROW NAIL FOR THE TREATMENT OF BONE FRACTURES ACCORDING TO THE MARROW CAVITY NAILING PROCEDURE AND MARROW NAIL TOOL

[75] Inventors: Curt Kranz, Berlin; Uve Sievers, Ludwigshafen, both of Fed. Rep. of Germany

[73] Assignee: Mecron Medizinische Produkte GmbH, Berlin, Fed. Rep. of Germany

[21] Appl. No.: 254,180

[22] Filed: Oct. 6, 1988

[30] Foreign Application Priority Data

Oct. 6, 1987 [DE] Fed. Rep. of Germany ....... 3734111

[51] Int. Cl.$^5$ ............................................. A61F 5/04
[52] U.S. Cl. ................................................... 606/62
[58] Field of Search ................. 623/16, 18, 20, 23; 606/62, 63

[56] References Cited

U.S. PATENT DOCUMENTS

| 3,893,196 | 7/1975 | Hochman | 606/62 |
| 3,977,398 | 8/1976 | Burstein | 606/62 |
| 4,446,857 | 5/1984 | Otte et al. | 606/62 |

FOREIGN PATENT DOCUMENTS

| 913228 | 6/1954 | Fed. Rep. of Germany | 606/62 |
| 2527460 | 1/1977 | Fed. Rep. of Germany | 606/62 |
| 3146065 | 5/1983 | Fed. Rep. of Germany | 606/62 |
| 1034730 | 8/1983 | U.S.S.R. | 606/62 |

Primary Examiner—David J. Isabella
Attorney, Agent, or Firm—Spencer & Frank

[57] ABSTRACT

A marrow nail for the treatment of bone fractures, including a marrow nail body having a hollow tubular cross section, the marrow nail body having a constricted marrow nail head, and a marrow nail tool for driving in, extracting and changing the position of the marrow nail during repositioning of a constricted marrow nail head. The marrow nail tool includes two generally parallel gripper jaws which are pivotable relative to one another, each of the two gripper jaws having a respective distal end which extends toward the other one respective distal end, a generally rectangular mandrel disposed between the two gripper jaws, and a securing ring which can be moved into a position encircling the two gripper jaws.

14 Claims, 4 Drawing Sheets

MARROW NAIL FOR THE TREATMENT OF BONE FRACTURES ACCORDING TO THE MARROW CAVITY NAILING PROCEDURE AND MARROW NAIL TOOL

CROSS REFERENCE TO RELATED APPLICATIONS

The subject matter of this application is related to that contained in copending U.S. Pat. application No. 07/254086 to Uve Sievers, entitled "MARROW NAIL FOR THE TREATMENT OF BONE FRACTURES", filed concurrently with the present application.

BACKGROUND OF THE INVENTION

The present invention relates to a marrow nail for the treatment of bone fractures according to a marrow cavity nailing procedure.

For example, the publication entitled "Die Bündel-Nagelung" [Bundle Nailing]published by Springer-Verlag, Berlin, Göttingen, Heidelberg, 1961, pages 3-26 and 56-58, discloses the procedure of marrow nailing and bundle nailing and describes various cross-sectional configurations of the marrow nails employed in this procedure. In addition to lack of bending and rotational stability of the prior art marrow nails, reference is made, in particular, to the numerous difficulties occurring when the marrow nails are removed after the fracture has healed and which, inter alia, lead to joint injuries and infections and frequently require the nail to be chiseled out.

The foregoing considerations apply as well for the use of so-called spring nails whose head ends are bent for future removal of the spring nail, are brought out of the location where they are driven in and must be gripped by a tool in the region of the respective bent head end for manipulation or removal of the spring nail. Due to these bent ends, however, such manipulation of the spring nails may cause movement of the bone which has been stabilized by the spring nail, which may then lead to injury to the bone at the point where the nails are driven in.

SUMMARY OF THE INVENTION

It is an object of the present invention to provide a marrow nail which exhibits high bending strength, rotational stability, low material fatigue, and which is relatively easily driven into bone marrow, so as to provide excellent stabilization of bone fragments, and wherein the marrow nail can be removed without difficulty and without substantial damage to the bone in which the marrow nail is disposed.

The above and other objects are accomplished according to the invention by the provision of a marrow nail for the treatment of bone fractures which includes a marrow nail body having a hollow tubular cross section, the marrow nail body having a constricted marrow nail head, and a marrow nail tool for driving in, extracting and changing the position of the marrow nail during repositioning of the constricted marrow nail head. The marrow nail tool includes two generally parallel gripper jaws which are pivotable relative to one another, each of the two gripper jaws having a respective distal end, each distal end extending toward the other respective distal end, a mandrel disposed between the two gripper jaws, and a securing ring which can be moved into a position encircling the two gripper jaws.

The invention also relates to a device for locally introducing force to nails which are composed of a plastic material without reducing the advantageous characteristics of the marrow nail or of an implant which is mounted by the marrow nail.

Particularly for nails made of a plastic material which is essentially adapted to be compatible with bone material, there exists the drawback that there is a relatively low limit to the magnitude of local forces introduced to the marrow nail during the driving-in of, and during the extraction of, the marrow nail. Those marrow nails which are composed only of plastic material tend to split or chip off, as does the natural bone material adjacent such a marrow nail which is composed only of plastic material.

In the present invention, the local introduction of force can be effected in an advantageous manner by means of a tool having a mandrel, the mandrel being insertable into the marrow nail to a depth corresponding to that of the position of the distal ends of the gripper jaws which grip and guide the marrow nail on both sides thereof, so that the material composing the marrow nail performs merely the function of a filler material in a sandwich-like composite (which includes the gripper jaws, the material composing the marrow nail, and the mandrel). Due to a constriction in the region of the head of the marrow nail, where the forces are introduced, the cross section of the entire arrangement including the jaws of the tool is not enlarged or is only insignificantly enlarged, in spite of the attached tool so that the freedom of movement remains during the introduction or extraction of the marrow nail.

An advantageous embodiment of the nail according to the present invention includes a thickened portion disposed at the end of the marrow nail head. This thickened portion is followed by a constricted portion which can be gripped by a tool, thereby making possible a secure grip for the extraction of the marrow nail even if only a slight transverse surface pressure can be exerted on the wall of the marrow nail head itself.

In an advantageous modification of the invention, the marrow nail has a cross section which is generally annular and which has generally circular inner and outer perimeters. The marrow nail has an end distal from the marrow nail head, this distal end having a tip which has a sharply ground, annular cutting edge.

In an advantageous embodiment, the marrow nail is composed of a tube formed of knit carbon fibers embedded in a hardenable synthetic resin. The tube may contain carbon fibers which are arranged so as to have crisscross interconnections, and the hardenable synthetic resin may be composed of a biocompatible TEEC matrix material in which the carbon fibers are embedded and which preferably hardens at a relatively high temperature of 380° C. The shape of the marrow nail head and of the distal end of the marrow nail according to the invention can be readily produced during fabrication of such fiber reinforced plastic nails, as discussed hereunder.

In a further advantageous embodiment, the marrow nail is bent in the shape of a C or J. In addition, the marrow nail can be provided with a metal force introduction element which is inserted, before hardening of the hardenable synthetic resin, into the marrow nail head. The metal force introduction element can be composed, for example, of a hollow cylinder whose interior wall has a rough surface. This element is preferably completely surrounded by the knit fiber fabric, before hardening of the hardenable synthetic resin, so that the metal force introduction element is secured to the marrow nail body in the region of the constricted portion. Since the metal force introduction element is relatively closely disposed to the marrow nail head, it interferes only slightly with the favorable body-compatible characteristics of the nail. If the nail is worked on in the body by means of bone working tools, as may be necessary during subsequent surgical procedures, during insertion of the marrow nail, and during connection thereof with a further prosthesis, the tapered distal end having a sharpened tip permits attachment to and removal of an additional element such as the further prosthesis. This further prosthesis can easily be removed as a whole without performing work on the metal force introduction element itself, so that only the pure plastic body remains in the bone marrow. In this event, another endoprosthesis component can then be connected to the marrow nail.

An advantageous embodiment of a marrow nail tool, for driving in, extracting and changing the position during repositioning of a constricted, hollow cylindrical marrow nail head or a flattened marrow nail head, has at least two circular segment-shaped gripper jaws which are pivotable relative to one another and which have inwardly extending ends to provide an abutment surface or edge which can securely grip an undercut formed beneath the head portion of the marrow nail. Additionally, the tool includes a cylindrical mandrel disposed generally in the center region between the gripper jaws for entering the marrow nail head, and a securing ring which can be pushed over the gripper jaws for securing the gripper jaws together about the marrow nail adjacent the undercut portion of the marrow nail head.

Another advantageous feature of a marrow nail tool according to the invention for driving in, extracting and changing the position during repositioning of a flattened marrow nail head, has two parallel gripper jaws which are pivotable relative to one another and whose ends extend toward one another the tool further including a rectangular or square mandrel disposed between the gripper jaws and a securing ring which can be pushed over the gripper jaws for securing the gripper jaws and the undercut portion of the marrow nail adjacent the marrow nail head.

In another embodiment, the marrow nail 1 has a hollow interior including a conically-widened portion. In this embodiment, a pin can be inserted into the hollow interior of the nail. The pin has jaws which are deformable outwardly so as to grip an interior constriction formed by the conically-widened portion of the marrow nail. This spreading engagement is preferably effected by driving in of a pin into the open end of the marrow nail. The tool inserts the pin by a gripper arrangement including two gripping ends connected respectively to two levers, the gripping ends and the levers being pivoted on opposed sides of a pivot point.

In another embodiment, the nail has a hollow interior including a conically-widened portion. In this embodiment, a pin can be inserted into the hollow interior of the nail. The pin has jaws which are biased spread outwardly and to grip behind the conically-widened region of the hollow interior of the nail. This spreading engagement is preferably effected by driving in of the pin from the one end of the nail. A tool having a pair of gripper jaws grips a projecting part of the nail. The tool inserts the pin by gripper arrangement including two gripping ends connected respectively to two levers, the gripping ends and the levers being pivoted on opposed sides of a pivot point.

The invention will be described in greater detail below with reference to embodiments which are illustrated in the drawings.

DETAILED DESCRIPTION OF THE PREFERRED EMBODIMENTS

Figure 1:
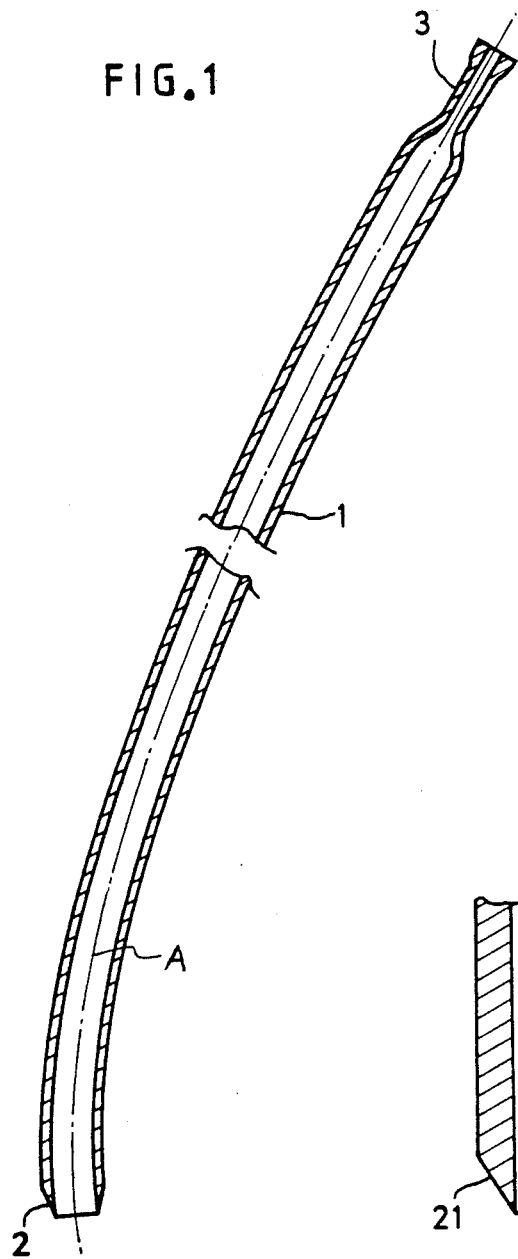
FIG. 1 is a longitudinal sectional view of a marrow nail according to the invention, composed of a carbon fiber reinforced plastic.

FIG. 1 is a longitudinal section taken through a tubular marrow nail 1 which is composed of carbon fiber reinforced plastic. As seen in FIG. 1, the marrow nail 1 has a longitudinal axis A which is slightly curved longitudinally generally in the shape of a C. The marrow nail 1 has a tip 2 as well as a constricted head 3. In the region of the tip 2, the diameter of the marrow nail 1 is about 10 mm. Preferably, the tubular marrow nail 1 has the shape of a hollow cylinder.

The carbon fiber reinforced plastic marrow nail 1 is manufactured starting with a tube of carbon fiber which is preferably knit in a crisscross fashion having many interconnections. This tube is then saturated with a hardenable plastic. The hardenable plastic is preferably composed of a biocompatible TEEC matrix material which embeds the carbon fibers and which hardens at a high temperature of preferably 380° C.

Alternatively, other materials can be used for the hardenable plastic, such as, for example, polyamide 6 or polyamide 6,6. Additionally, materials can be used which are customarily referred to as bulk plastics, such as, for example, polyolefins (polyethylene, polypropylene). In conjunction with the carbon fibers according to the invention, this produces a high strength marrow cavity nail 1 which is distinguished by high tensile strength and stiffness as well as high heat resistance. These qualities are ordinarily associated only with metal materials; however, the aforementioned characteristics of the novel nail 1 can even exceed the corresponding characteristics of a similar nail made of a metal material.

The C or J shape of the marrow nail 1 can be obtained by the introduction of a suitable core in the form of, for example, a cylindrical wire having the corresponding outer diameter, and around which the knit tube of carbon fibers is formed or drawn. After application and hardening of a suitable synthetic resin, the core (not shown) can be removed and the marrow nail 1 made of carbon fiber reinforced plastic can be worked further.

To obtain a smooth surface for the marrow nail 1, the hardenable synthetic resin can be applied under high pressure, or alternatively the surface of the marrow nail 1 may subsequently be polished.

The use of a carbon fiber reinforced plastic material for the production of a marrow nail 1, in conjunction with formation of a suitable diameter of the marrow nail 1, ensures that when the marrow nail 1 is driven into the marrow cavity of a bone, it is possible to guide the marrow nail 1 accurately from its point of entry in the bone without bending of the marrow nail 1 and without the marrow nail 1 having uncontrolled movements. The tip 2 of the marrow nail 1 has a sharply ground annular cutting edge which permits driving in of the marrow nail 1 with little force while avoiding crushing of bone marrow during the driving-in process.

When the marrow nail 1 is inserted in the bone, it is distinguished by its high rotational stability and its ability to absorb even the strongest vibrations without material fatigue. A further advantage is its good tissue compatibility and the avoidance of any negative influences on the bone marrow such as may occur, for example, in conjunction with a steel nail due to corrosion. The cylindrical, slightly bent shape of the marrow nail 1, in conjunction with its selected diameter, permits secure contact of the marrow nail 1 in the marrow cavity of the bone and thereby provides the prerequisite characteristics necessary for a marrow nail used for the stabilization of bone fragments, when only a single marrow nail is used.

Extraction of the marrow nail 1 when the fracture is healed can be performed easily by gripping the constricted or flattened head 3 of the marrow nail 1, without the danger of the marrow nail 1 breaking off, since the marrow nail 1 is composed of a fiber material which is bonded together, rather than metal which tends to brea relatively easily.

Figure 2:
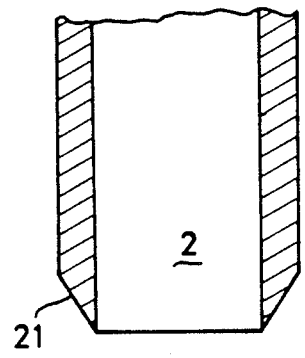
FIG. 2 is an enlarged illustration of the tip of the marrow nail of FIG. 1.

FIG. 2 shows, at an enlarged scale, the tip 2 of the marrow nail 1 and clearly shows a conically, slightly tapered outer face 21 of the tip 2. This outer face 21 is created preferably by sharp grinding of the tip 2, so as to thereby create an annular cutting edge.

Figure 3:
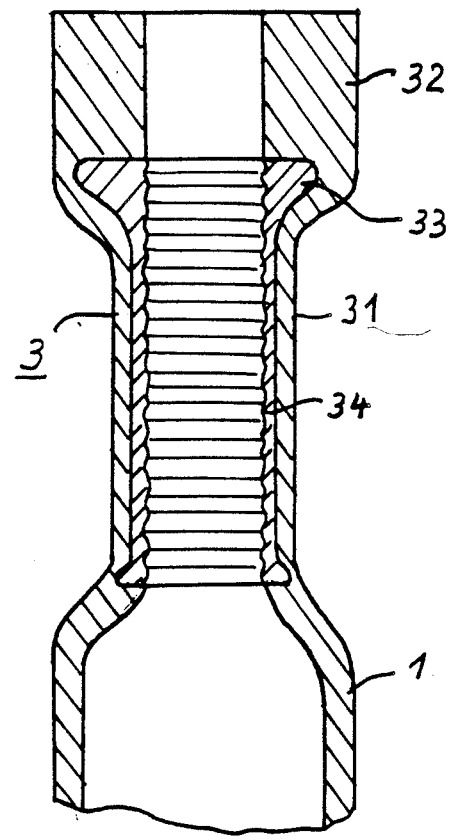
FIG. 3 is an enlarged view of the marrow nail head of FIG. 1.

FIG. 3 shows, to an enlarged scale, the marrow head 3 which is composed of a cylindrically constricted or flattened portion 31 and an outwardly thickened, bent or crimped end piece 32, hereinafter referred to as relatively enlarged portion 32. A metal force introducing element 34 in the form of a hollow cylinder of titanium in this embodiment is inserted into the head 3 in the region of the constricted portion 31 before that portion is constricted to form its final shape, namely that of the cylindrically constricted or flattened portion 31. The interior surface of the force introducing element 33 is roughened, preferably in the form of parallel grooves or threaded grooves so that head 3, and with it the entire marrow nail 1, can be pulled out of the marrow cavity in which it has been inserted by the gripping thereof with a suitable tool, for example a forceps, in a force-locking manner for extraction of the marrow nail 1 from the marrow cavity or to change the position of the tip 2 of the nail 1 for repositioning of the marrow nail 1.

Additionally, the constricted or flattened head 3 of the hollow cylindrical marrow nail 1 can also facilitate the attachment of a suitable tool which is to be used for driving the marrow nail 1 into the marrow cavity of a bone.

The metal force introducing element 34 may be inserted, prior to formation of the final marrow nail 1, into the fabric of carbon fibers when the marrow nail 1 is being manufactured. The force introducing element 34 can therefore be bonded to the plastic used to coat the carbon fibers so that, during hardening of the plastic, a firm bond occurs between the plastic-and-carbon-fiber portion of the marrow nail head 3 with the metal force introducing element 34.

Figure 4:
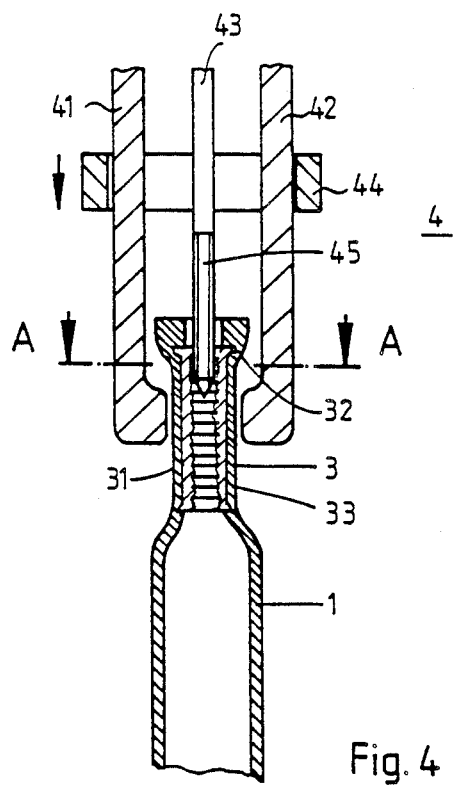
FIG. 4 is a longitudinal sectional view of the marrow nail head of FIG. 1, together with a marrow nail removal tool.

As shown in FIG. 4, a marrow nail tool 4 includes two gripper jaws 41 and 42 which are articulated about a common pivot axis (not shown), and which are therefore pivotable relative to one another. The gripper jaws 41 and 42 are shaped to extend inwardly at their lower ends distal from the pivot axis (not shown) and, by engagement with the constricted portion of the marrow nail head 3 adjacent the constricted portion 3, the gripper jaws 41 and 42 also thereby grip an undercut formed between the constricted portion 31 and the relatively enlarged portion 32. This gripping action of the gripper jaws 41 and 42 of the marrow nail tool 4 thereby reliably permits sufficient force to be applied to the marrow nail 1 to cause it to be pulled out of the marrow cavity of the treated bone.

When the mandrel 43 is screwed in, a self-cutting thread 45 disposed thereon cuts into the interior of the constricted region of the nail so that an even better locking engagement can be realized. The thread 45 is partially indicated in FIG. 4 by dashed lines. If such a self-cutting thread is employed, it may be possible to omit a metal sleeve of such as the force introducing element 34. In this case, the thread 45 must have such dimensions that it will not cut through the fibers of the marrow nail 1. This can be realized by reducing the sharpness of the outer thread edges so that this thread portion produces only blunt grooves but does not cut into the nail material in a destructive manner.

To center the marrow nail tool 4 and to improve the force transmission from the tool 4 to the constricted marrow nail head 3, a centrally disposed mandrel 43 is provided. In the attached state of the marrow nail tool 4, the mandrel 43 is engaged in the central, hollow region of the cylindrically constricted portion 31. To change the position of, or to extract the marrow nail 1, the gripper jaws 41, 42 of the tool 4 are placed against the outside surface of the constricted portion 31 on the marrow nail head 3 and then a securing ring 54 is displaced downwardly as seen in FIG. 4 to cause the inwardly extending ends of the gripper jaws 41 and 42 to lie firmly against the outer surface of the constricted marrow nail head 3 at a location which is beneath the aforementioned undercut.

The presence of the metal force introducing element 33 in the constricted marrow nail head 3 serves to increase the friction lock with the mandrel 43 during application of the tool 4 to the marrow nail 1, so that the marrow nail 1 can be reliably extracted.

Figure 5:
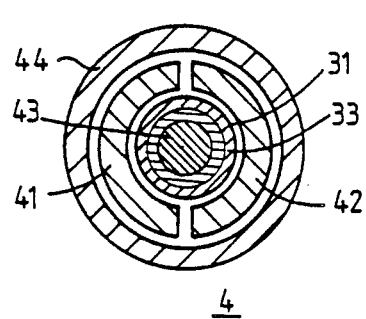
FIG. 5 is a cross-sectional view of a constricted marrow nail head according to the invention, together with a marrow nail tool, as taken along line 5—5 of FIG. 4.
Figure 6:
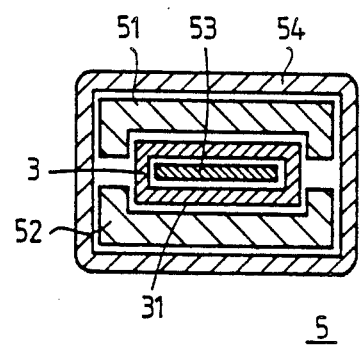
FIG. 6 is a cross-sectional view of a flattened marrow nail head according to the invention with an attached marrow nail tool, as would be seen if taken along a line similar to line A—A of FIG. 4.

The marrow nail tool 4 can have different configurations. For example, the tool 4 can have different corresponding elements in dependence on whether marrow nail head 3 is formed to have a constricted shape or a flattened shape. For example, the FIG. 5 is a cross-sectional view as taken along line A—A of FIG. 4 of a suitable marrow nail tool 4 for use with a marrow nail head 3 which has a constricted, cylindrical shape. FIG. 6 is a cross-sectional view of another embodiment of a suitable marrow nail tool 5 for use with a flattened marrow nail head 3', as would be seen if the nail head 3' were present in FIG. 4 and the section were taken along line A—A of FIG. 4.

In the embodiment shown in FIG. 5, the marrow nail tool 4 is composed of two semicircular gripper jaws 41 and 42 which, in an installed state, grip the region of the tubular marrow nail 1 which is adjacent the constricted portion 31 of the marrow nail head 3. A mandrel 43 is inserted within the constricted portion 31 to center the tool 4 and increase the maximum pressure which can be applied to create a force lock against the constricted marrow nail head 3.

The semicircular gripper jaws 41 and 42 are then firmly enclosed by proper positioning the securing ring 44 so that the gripper jaws lie tightly against the outer surface of the constricted portion 31 of the constricted head 3.

In the embodiment where a flattened marrow nail head 3' is used, as shown in FIG. 6, the pair of gripper jaws 51 and 52 of the marrow nail tool 5 U-shaped and surround the flattened outer surface of the constricted portion 31' of the flattened marrow nail head 3'. In this embodiment, the mandrel 53 has a rectangular cross section and engages in the interior of the flattened marrow nail head 3' which, analogously to the cylindrical embodiment, may be provided with a flat, metal force introducing element (not shown in FIG. 6) to increase the force lock applied by the tool 5.

Around the U-shaped gripper jaws 51 and 52 there is displaceably disposed a hollow rectangular securing ring 54 which secures the gripper jaws 51 and 52 in an installed state of the tool 5.

Other embodiments of the marrow nail tool are also possible. For example, instead of employing two semi-circular gripper jaws, a plurality of circular segment-shaped gripper jaws can also be employed. Moreover, it is possible to employ a securing ring that can be screwed on instead of the illustrated slideably displaceable securing ring, in which case the gripper jaws must be provided with a corresponding external thread.

To facilitate rotation of the marrow nail 1 during repositioning, the constricted portion 31 of the marrow nail head 3, as well as the constricted portion 31' of the marrow nail head 3' of the embodiment shown in FIG. 6, may be provided with longitudinally-disposed grooves or the like, in which case the inwardly bent ends of the gripper jaws should be provided with corresponding longitudinal grooves.

Figure 7:
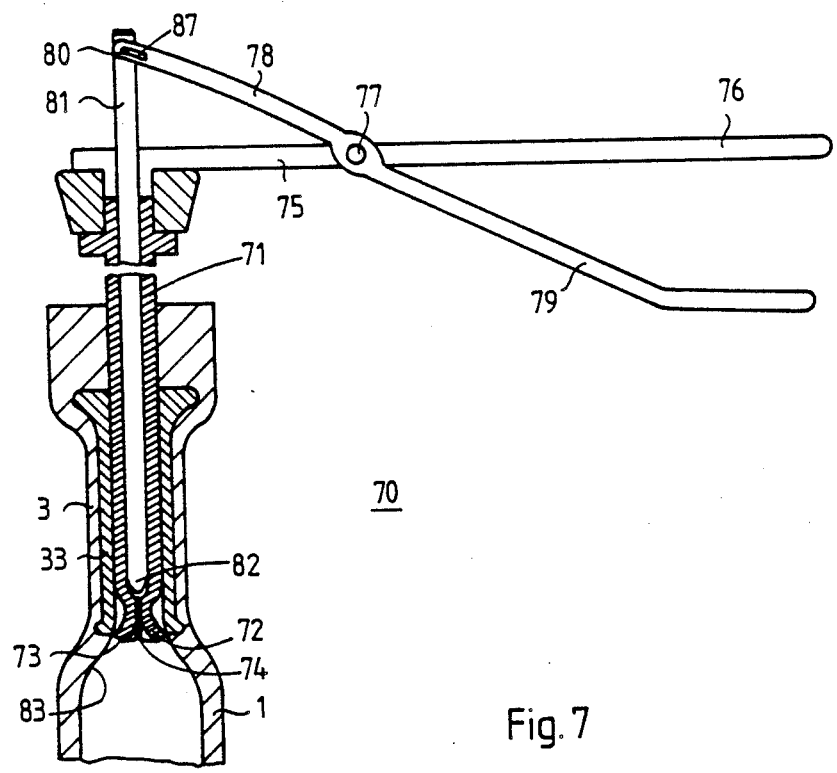
FIG. 7 is a side view in section of a marrow nail, together with a marrow nail tool shown partially in section, according to the invention.

In the embodiment shown in FIG. 7, a tool 70 for manipulating the nail includes an elongated hollow element 71 having outwardly oriented jaws 72 and 73 at its ends to be introduced into the marrow nail 1. However, the tubular body of the element 71 is tapered toward the end equipped with the jaws 72 and 73 so that the total diameter including the outwardly oriented jaws 72 and 73 does not exceed the total inner diameter of the marrow nail 1. However, the parts of the element 71 equipped with the jaws 72 and 73 can be spread open, which is made possible by slots provided between the jaws 72 and 73. One slot 74 can be seen in FIG. 7. Element 71 is connected by way of a lever 75 with a gripping end 76, and a pivot pin 77 is provided between the lever 75 and the gripping end 76. Here, another lever 78 is pivotably mounted about the pivot pin 77 and is equipped with a gripping end 79.

The levers 75 and 78 having the respective ends 7 and 79, together with the pivot pin 77, form a forceps-like instrument. At the end of the lever 78 is a spreading pin 81 which is connected to the lever 78 by a pin 80 which is confined to slide within an elongated slot 79. The pin 80 passes through the spreading pin 81 transversely, and is thereby connected with the lever 78 such that, when the gripping ends 76 and 79 are pressed together, the spreading pin 81 is pressed into the element 71.

Figure 8:
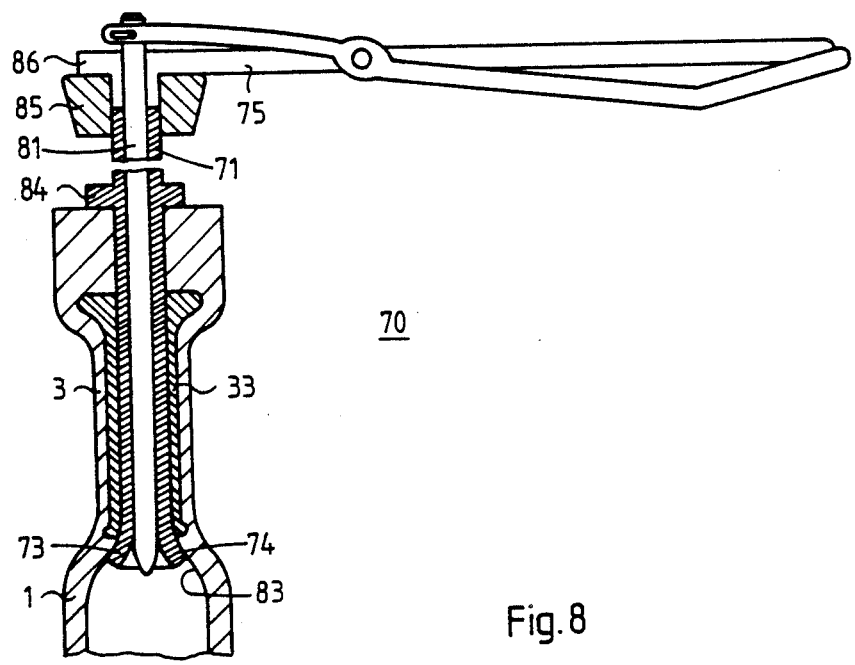
FIG. 8 is a side view in section of a marrow nail, together with a marrow nail tool having an extension shown partially in section, according to the invention.

The spreading pin 81 has a tip 82 which can be pressed into the region of the jaws 72 and 73 to spread them apart once the jaws 72 and 73 have reached a conically widened region 83 of the interior of the marrow nail 1. This position is shown in FIG. 8. Once spread outwardly, the jaws 72 and 73 grip behind the widened region 83 and thereby provide for secure anchorage against pulling out of the pin 81. As a result of this locking engagement of the pin 81 and the marrow nail 1, it is possible for the tool 70 to manipulate the marrow nail 1.

FIG. 8 shows an annular extension 84 which, when the 72 and jaws 73 are spread open into engagement with the marrow nail 1, is disposed on the element 71 adjacent the head end of the marrow nail 1, ensures reliable force transmission in the direction of applied pressure and extraction forces. The shaft of the hollow element 71 can be made substantially longer than indicated in FIG. 8. In this case, a striking member 85 is disposed so as to be slidably displaceable on the hollow element 71 of the tool 70. The striking member 85 can be manipulated along the hollow element 71 on the lever 75 and its extension 86 beyond the spreading pin 81 such that it strikes the extension 86, imparting an impulse force thereto and thereby serving to drive out the marrow nail 1. The force introducing element 34 serves to reinforce the constricted region 3 of the nail. Since the plastic fiber reinforced nail body of the marrow nail 1 is suitable in every way for the transfer of extraction and pressure forces, this element 34 may also be omitted.

The present invention is not limited in its embodiments to the above-described preferred embodiment. For example, an external thickened portion and a constriction of the inner cross section of the marrow nail 1 in its head region need not be present simultaneously. Each one of these features is sufficient for engagement with a corresponding tool. If, however, both features are present at a nail end, this marrow nail 1 can be gripped equally well with different tools.

The present disclosure relates to the subject matter disclosed in German Application No. P 37 34 111.1 of Oct. 6, 1987, the entire specification of which is incorporated herein by reference.

It will be understood that the above description of the present invention is susceptible to various modifications, changes, and adaptations, and the same are intended to be comprehended within the meaning and range of equivalents of the appended claims.

What is claimed is:

1. An elongated intramedullary nail for repair of a bone fracture, said nail comprising a hollow tubular body terminating at opposite ends, and said tubular body adjacent one end thereof having a constricted cross section forming a nail head for engaging a surgical tool.

2. A marrow nail as defined in claim 1, wherein said one end has a thickened end portion.

3. A marrow nail as defined in claim 1, wherein said marrow nail body, including said marrow nail head, is composed of carbon fiber reinforced plastic.

4. A marrow nail as defined in claim 1, wherein said marrow nail body comprises a tubular, carbon fiber reinforced plastic body which is slightly curved along its longitudinal direction; and further comprising a tip having a free end disposed at an end of said marrow nail body distal from said marrow nail head, said tip having an outer surface which is conically tapered toward said free end so as to terminate in an annular cutting edge.

5. A marrow nail as defined in claim 4, wherein said annular cutting edge has a hollow cylindrical crosssection.

6. A marrow nail as defined in claim 4, wherein said tubular, carbon fiber reinforced plastic body includes a tube knit of carbon fibers embedded within a hardenable synthetic resin.

7. A marrow nail as defined in claim 6, wherein said tubular, carbon fiber reinforced plastic body includes carbon fibers which are disposed so as to have a plurality of cross-wise interconnections.

8. A marrow nail as defined in claim 6, wherein said hardenable synthetic resin is a biocompatible TEEC matrix material in which the carbon fibers are embedded and which preferably hardens at a temperature of approximately 380° C.

9. A marrow nail as defined in claim 1, wherein said marrow nail body has a longitudinal axis having a generally C-shaped curvature.

10. A marrow nail as defined in claim 1, further comprising a separate metal force introducing element embedded in said constricted marrow nail head.

11. A marrow nail as defined in claim 10, wherein said metal force introducing element comprises a hollow cylinder having an inner wall which has a rough surface.

12. A marrow nail as defined in claim 11, wherein said rough surface has a plurality of radial grooves therein.

13. A marrow nail as defined in claim 10, wherein said metal force introducing element is composed of titanium.

14. A marrow nail as defined in claim 11, wherein said rough surface has threading therein.

* * * * *